United States Patent [19]

Bornzin

[11] Patent Number: 4,502,492
[45] Date of Patent: Mar. 5, 1985

[54] LOW-POLARIZATION LOW-THRESHOLD ELECTRODE

[75] Inventor: Gene A. Bornzin, Coon Rapids, Minn.

[73] Assignee: Medtronic, Inc., Minneapolis, Minn.

[21] Appl. No.: 489,657

[22] Filed: Apr. 28, 1983

[51] Int. Cl.³ .............................................. A61N 1/04
[52] U.S. Cl. .................................... 128/785; 128/786
[58] Field of Search ................................. 128/784–786, 128/419 P, 642

[56] References Cited

U.S. PATENT DOCUMENTS

| 3,749,101 | 7/1973 | Williamson | 128/786 |
| 3,935,864 | 2/1976 | Lagergren | 128/786 |
| 4,149,542 | 4/1979 | Thoren | 128/786 |
| 4,437,474 | 3/1984 | Peers-Trevarton | 128/786 |

FOREIGN PATENT DOCUMENTS 64289 11/1982 European Pat. Off. ........ 128/419 P

OTHER PUBLICATIONS

Zeuthan, "Potentials and Small Signal . . . ", Med. & Biol. Eng. & Comput., Sep. 1978, 16/No.5, pp. 489–499.

Primary Examiner—Lee S. Cohen
Attorney, Agent, or Firm—Reed A. Duthler; Joseph F. Breimayer; John L. Rooney

[57] ABSTRACT

A low-polarization electrode for use in medical stimulation leads. The electrode is provided with grooving and is coated with platinum black.

7 Claims, 6 Drawing Figures

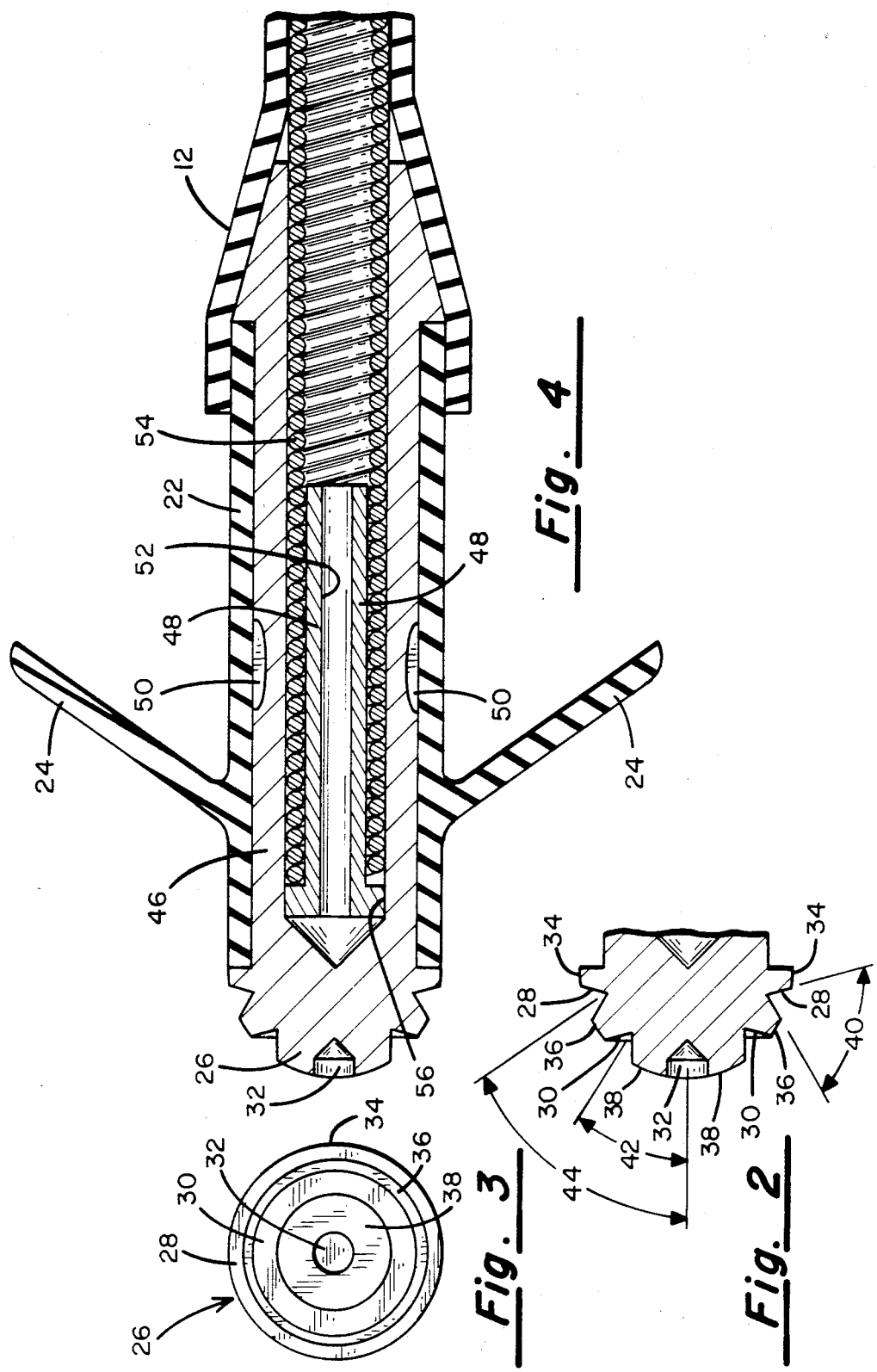

LOW-POLARIZATION LOW-THRESHOLD ELECTRODE

BACKGROUND OF THE INVENTION

This invention relates generally to medical electrical leads and, in particular, to cardiac pacing leads.

During the past twenty years, the technology of cardiac pacing has significantly advanced, with implantable pacemakers displaying an ever-increasing variety of pacing modalities, substantially broadening the indications for pacemaker use. In conjunction with this advancement, there has been extensive research and development effort expended to optimize the performance of pacing leads. As a result, a number of desirable performance characteristics for pacemaker leads have been identified.

It is generally agreed that an optimal pacing electrode will yield a low threshold of stimulation and will be responsive to the small electrical signals naturally generated by the heart. It is also known that polarization of the electrode structure by stimulation pulses may interfere with efficient delivery of these stimulation pulses. The effect is discussed in detail in U.S. Pat. No. 3,476,116 issued to Parsonett et al. Parsonett addresses this problem by use of a large surface area electrode within a fluid-filled chamber provided with a small aperture through which the stimulation energy must pass. A somewhat different approach is disclosed in U.S. Pat. No. 3,749,101 issued to Williamson. Williamson limits the stimulation area of the electrode to a small portion of the electrode body and fabricates that portion of platinum coated with platinum black, claiming an electrode having reduced polarization. A third approach is disclosed in U.S. Pat. No. 4,156,429 issued to Amundson. Amundson employs a metallic filamentous structure to produce a pacing electrode. This structure is claimed to reduce the energy required for stimulation over extended periods of time, as a result of a reduction in polarization and of improved biocompatability.

SUMMARY OF THE INVENTION

The present invention is a cardiac pacing lead employing an electrode which has a novel geometry and which is provided with a coating of platinum black. The electrode is generally hemispherical and is provided with grooving. In its preferred embodiment, the electrode is provided with circular grooves and with tines which urge the electrode into contact with the endocardial wall, in a direction roughly perpendicular to the grooves. The electrode may be constructed of platinum or of a conductive base metal provided with an external surface of platinum and is preferably coated over its external surface with a coating of platinum black. The grooving of the electrode provides areas of small radius of curvature which contact the endocardial surface, resulting in localized increases in current density at the edges of the grooves. The hemispherical shape of the electrode maximizes the opportunity for contact between the groove edges and the endocardium. In its preferred embodiment, the electrode displays extremely low polarization following the application of a stimulation pulse and thereby displays significantly enhanced ability to sense the natural electrical activity of the heart.

As discussed above, there has been significant effort directed to reducing electrode polarization to a level which does not interfere with the delivery of stimulation impulses. However, many presently available electrodes known to applicant still display some polarization following a stimulation pulse. This polarization dissipates following the stimulation pulse and is not believed to significantly interfere with the delivery of the following stimulation pulses. However, polarization of these electrodes is believed sufficient to interfere with the ability of the electrode to respond to the electrical activity of the heart during the period immediately following delivery of the stimulation impulse. This does not prevent proper functioning of presently available pacemakers, as they are typically refractory to any natural electrical activity within the heart during the period immediately following a stimulation pulse. However, as pacemakers having modes of operation intended to regulate tachycardias and other arrythmias are developed, it is anticipated that the ability to sense heart activity immediately following the stimulation pulse will be a desirable characteristic. In particular, this ability would allow the development of a pacemaker capable of determining whether its stimulation pulses have successfully triggered the desired heart activity. The present invention provides an electrode having this desirable ability.

The details of the present invention and of its advantages may be more fully understood in conjunction with the attached drawings and the following detailed description.

BRIEF DESCRIPTION OF THE DRAWINGS

FIG. 2 shows a cross sectional view of the distal tip of the electrode of the lead shown in FIG. 1.

FIG. 3 shows a front plan view of the distal tip of the electrode of the lead shown in FIG. 1.

FIG. 4 shows a cross sectional view of the distal portion of the pacing lead shown in FIG. 1.

DETAILED DESCRIPTION OF THE DRAWINGS

Figure 1:
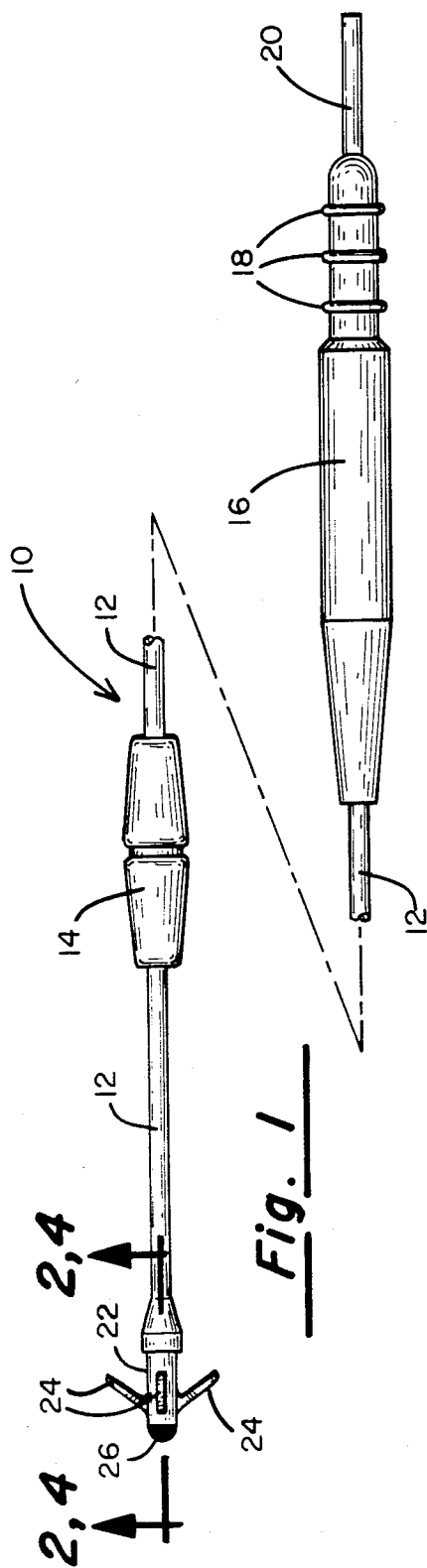
FIG. 1 shows a side plan view of a pacing lead according to the present invention.

FIG. 1 shows a side plan view of a pacing lead according to the present invention. The lead is provided with an elongated lead body 10 which is covered with an insulation sheath 12, which may be fabricated of silicone rubber, polyurethane or other suitable plastic. At the proximal end of lead body 10 is connector assembly 16, which is provided with sealing rings 18 and which carries connector pin 20. Connector assembly 16 may be constructed using techniques known to the art, and may be fabricated of silicone rubber, polyurethane or other suitable plastic. Connector pin 20 may be fabricated of stainless steel or other conductive material. At the proximal end of lead body 10 is electrode 26 which is discussed in more detail below. Immediately proximal to the exposed portion of electrode 26 is tine sheath 22 which bears four tines 24, of which three are visible. Tines 24 engage with heart tissue and urge electrode 26 into contact with the endocardium, in a direction parallel to the lead axis. Tines 22 are more fully described in U.S. Pat. No. 3,902,501, issued to Citron et al, incorporated herein by reference. Slideably mounted around lead body 10 is fixation sleeve 14, which serves to stabilize the lead at the site of veinous insertion. Sleeve 14 is more fully described in commonly assigned U.S. application Ser. No. 297,469 by White.

FIG. 2 shows a cross sectional view of the distal end of electrode 26 shown in FIG. 1. Electrode 26 is generally hemispherical and is provided with two circular, v-shaped grooves 28 and 30 and with an axial bore 32. Grooves 28 and 30 and bore 32 divide the outer most surface of electrode 26 into three annular areas 34, 36 and 38. Central bore 32 and groove 28 define an angle 44, which may be 70 degrees. Central bore 32 and groove 30 define an angle 42 which, may be 40 degrees. Grooves 28 and 30 are cut having an angle 40 which may be 60 degrees. The edges defined by the grooves and annular areas of electrode 26 are seen to provide areas of small radius of curvature, which are believed to provide localized increases in current density and to thereby reduce stimulation thresholds. Precise adherence to the dimensions given above is not believed necessary to practice the invention. However, it is desirable that the edges defined by the grooves and annular areas display a small radius of curvature, for the reasons discussed above. Arranging the grooving generally perpendicular to the direction in which the tines urge the electrode is believed to be beneficial. In the preferred embodiment this is accomplished using circular grooves. The grooves are believed to assist in fixation of the electrode to the endocardium by providing invaginatons into which tissue may grow. Such fixation is believed to reduce the possibility of micro-dislodgments, which can cause an increase in threshold due to irritation of the endocardium, increased fibrotic growth, or simply due to the displacement of the electrode from the endocardium.

FIG. 3 shows a front plan view of the distal tip of electrode 26. In this view, the form of annular areas 36 and 38 is more clearly apparent, along with the circular form of grooves 28 and 30.

FIG. 4 shows a cross sectional view of the distal end of the lead of FIG. 1. In this view, electrode 26 is seen to be provided with an elongated tubular portion 46 which has a central lumen 56. Mounted within lumen 56 are swaging pin 48 and coiled conductor 54. Crimps 50 maintain coiled conductor 54 tightly fixed between swaging pin 48 and tubular portion 46 of electrode 26. This structure provides mechanical and electrical coupling of conductor 54 to electrode 26. Coiled conductor 54 extends proximally within insulating sheath 12 to the proximal end of the lead and is coupled to connector pin 20 (FIG. 1). Swaging pin 48 is provided with a central lumen 52 into which a stylet may be inserted. Coiled conductor 54 may be fabricated of MP35N alloy or other suitable conductive material, and is preferably a multifilar coil. Swaging pin 48 may be fabricated of stainless steel or other appropriate metal. Electrode 26 is preferably constructed of or provided with a coating of platinum or of a platinum alloy, but may also be constructed of titanium, rhodium, irridum, or alloys thereof.

The exterior surface of electrode 26 is preferably completely covered with a coating of platinum black, which allows for a substantial reduction in electrode polarization. In order to assure good adhesion of the platinum black to the preferred platinum electrode surface, the electrode should be cleaned by first soaking the electrode in aqua regia, subsequently boiling the electrode in fuming hydrochloric acid, and finally sandblasting the exterior surface of the electrode to remove any oxidation. After such cleaning, the electrode may be platinized by immersing the electrode, as cathode, in a platinizing solution consisting of 3% Platinum chloride dissolved in 0.025% lead acetate solution. An anode of inert metal may then be placed into the platinizing solution and a sufficient current passed through the cell so that small bubbles are visible at the electrode. The process should be continued until a layer of platinum black is deposited over the entire electrode. The above process for cleaning and platinizing produces a platinum black surface which is sufficiently durable for use on the exposed annular portions 34, 36, and 38 of the electrode, which directly contact the endocardium as well as within grooves 28, 30 and hole 32.

It is believed that platinum black, which has a microporous surface of submicron size particles, is less easily recognized by the body's immunological system as a foreign body allowing for the formation of a thinner fibrotic capsule surrounding the electrode. A thinner capsule allows the electrode to remain in close proximity to stimulatable heart tissue which is believed to increase the current density to the stimulatable tissue and thereby lower stimulation thresholds. In the preferred embodiment of the invention, the entire exterior of electrode 26 is coated, although coating only the grooves of the electrode is also believed to offer some benefits. In addition, coating of the entire exposed surface of the electrode is believed to offer benefits for electrode geometries other than that of the preferred embodiment.

Figure 5:
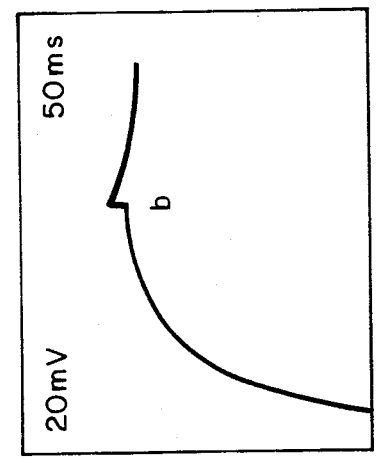
FIG. 5 illustrates an oscilloscope tracing which depicts the performance of the presently available pacing electrode.

FIG. 5 illustrates an oscilloscope trace depicting the actual performance of a currently available pacing lead, the Medtronic ® Model 6971 Tined Pacing lead. This lead is similar to the lead illustrated in FIG. 1 in all respects except for the electrode, which is a platinum ring tip electrode of the type widely used for cardiac pacing. The tracing is taken from such a lead implanted within a living dog heart, and illustrates the electrical potential across the electrode following a stimulation impulse by am external, A-V sequential pacemaker. In this tracing, the scale is such that the screen encompasses a range of 160 millivolts vertically, and 500 milliseconds horizontally. The stimulation impulse, not visible in the tracing, occurs at point A, after which the electrode can be seen to gradually depolarize. Although the dog heart does respond to the stimulus pulse, no evidence of that response is present in the tracing, because the natural electrical activity of the dog heart which would otherwise indicate the response is overwhelmed by the repolarization of the electrode. The artifact at point B is due to the atrial output of the pacemaker.

Figure 6:
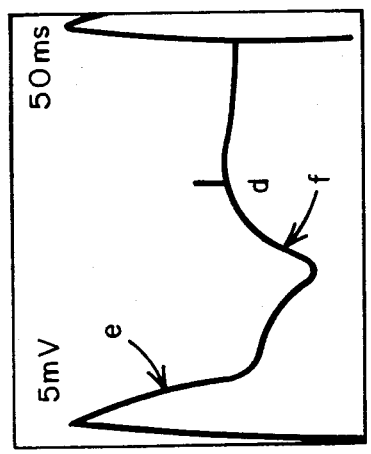
FIG. 6 illustrates an oscilloscope tracing which depicts the performance of an electrode constructed according to the present invention.

FIG. 6 illustrates an oscilloscope trace depicting the actual performance of the preferred embodiment of the present invention, as shown in FIGS. 1 through 4, in which the electrode is completely covered with platinum black. The tracing is taken from a lead implanted within a living dog heart and illustrates the electrical potential across the electrode following a stimulation pulse by an external, A-V sequential pacemaker. In this tracing, the scale is such that the screen encompasses a range of 40 millivolts vertically and 500 milliseconds horizontally. Clearly discernable at E is the QRS complex indicative of the ventricular contraction of the dog heart, followed at F by the T-wave indicating repolarization of the dog heart. The stimulation pulse, located at point C, is not visible in this tracing. This tracing clearly depicts the ability of an electrode according to the present invention to sense the natural electrical heart activity generated in response to a stimulation pulse. This ability to sense immediately following a stimulation pulse is believed to result from the extremely low polarization of the electrode, and the resultant very rapid discharge of that polarization. As such, the invention provides an electrode which is capable of sensing whether a stimulation pulse has actually resulted in a heart beat. The artifact at point D is caused by the atrial output of the pacemaker.

The invention has been described in detail with particular reference to the preferred embodiment thereof, but it will be understood that variations and modifications can be effected within the scope of the invention.

What is claimed is:

1. An implantable lead, comprising:
   an electrical conductor having a proximal end and a distal end;
   an insulative sheath covering said conductor;
   an electrical connector coupled to the proximal end of said conductor; and
   an electrode means having a surface exposed through the exterior of said insulative sheath, for directly contacting the endocardium of a human heart at said exposed surface, wherein substantially all of said exposed surface is provided with a coating of platinum black and wherein said electrode means is coupled to the distal end of said conductor.

2. An implantable lead according to claim 1 wherein said exposed surface of said electrode means is platinum.

3. An implantable lead according to claim 2 wherein said electrode means is fabricated of platinum.

4. An implantable lead according to claim 1 wherein the exposed surface of said electrode means has grooving.

5. An implantable lead according to claim 4 wherein the exposed surface of said electrode means is generally hemispherical.

6. An implantable lead, comprising:
   an electrical conductor having a proximal end and a distal end;
   an insulative sheath covering said conductor;
   an electrical connector coupled to the proximal end of said conductor; and
   an electrode coupled to the distal end of said conductor and having an exposed surface, said electrode provided with tine means for urging said exposed surface of said electrode in a predetermined direction, said exposed surface of said electrode provided with grooving perpendicular to said predetermined direction.

7. An implantable lead comprising:
   an electrical conductor having a proximal end and a distal end;
   an insulative sheath covering said conductor;
   an electrical connector coupled to the proximal end of said conductor; and
   an electrode coupled to the distal end of said conductor, said electrode having an exposed surface having a generally hemispherical shape, said exposed surface provided with concentric cirular grooving.

* * * * *

UNITED STATES PATENT AND TRADEMARK OFFICE
CERTIFICATE OF CORRECTION

PATENT NO. : 4,502,492
DATED : 5 March 1985
INVENTOR(S) : Gene A. Bornzin

It is certified that error appears in the above—identified patent and that said Letters Patent are hereby corrected as shown below:

Claim 1,
    line 7, "through" should be --to--;

Claim 7,
    line 10, "cirular" should be --circular--.

Signed and Sealed this

Sixth Day of August 1985

[SEAL]

Attest:

DONALD J. QUIGG

Attesting Officer     Acting Commissioner of Patents and Trademarks